(12) United States Patent
Callahan et al.

(10) Patent No.: US 7,918,835 B2
(45) Date of Patent: Apr. 5, 2011

(54) COMPLIANT GUARD FOR USE WITH AN ASPIRATION INSTRUMENT

(75) Inventors: Mark J. Callahan, Wilbraham, MA (US); Mark S. Guitarini, Amherst, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 93 days.

(21) Appl. No.: 11/507,212

(22) Filed: Aug. 21, 2006

(65) Prior Publication Data
US 2008/0045885 A1 Feb. 21, 2008

(51) Int. Cl.
*A61M 5/00* (2006.01)
(52) U.S. Cl. .......... 604/263; 604/35; 604/118; 604/268
(58) Field of Classification Search .................. 604/35, 604/73, 313, 192–298, 110, 57–64
See application file for complete search history.

(56) References Cited

U.S. PATENT DOCUMENTS

| | | | |
|---|---|---|---|
| 3,101,543 A * | 8/1963 | Baughan | 433/94 |
| 3,430,631 A | 3/1969 | Abramson | |
| 3,528,427 A * | 9/1970 | Sheridan et al. | 604/45 |
| 3,864,831 A * | 2/1975 | Drake | 433/91 |
| 4,204,328 A | 5/1980 | Kutner | |
| 4,228,798 A | 10/1980 | Deaton | |
| 4,708,717 A | 11/1987 | Dean et al. | |
| 4,872,837 A | 10/1989 | Issalene et al. | |
| 4,886,492 A | 12/1989 | Brooke | |
| 4,915,691 A | 4/1990 | Jones et al. | |
| 4,932,952 A | 6/1990 | Wojciechowicz, Jr. | |
| 4,950,247 A | 8/1990 | Rosenblatt | |
| 4,981,473 A | 1/1991 | Rosenblatt | |
| 5,002,534 A | 3/1991 | Rosenblatt | |
| 5,029,580 A | 7/1991 | Radford | |
| 5,045,075 A | 9/1991 | Ersek | |
| 5,085,633 A * | 2/1992 | Hanifl et al. | 604/35 |
| 5,125,909 A | 6/1992 | Heimberger | |
| 5,151,094 A * | 9/1992 | Hanifl | 604/118 |
| 5,360,414 A | 11/1994 | Yarger | |
| 5,380,245 A | 1/1995 | Reiterman et al. | |
| 5,464,397 A | 11/1995 | Powers, Jr. | |
| 5,522,826 A | 6/1996 | Daily | |
| 5,542,929 A | 8/1996 | Laabs et al. | |
| 5,562,077 A | 10/1996 | Schultz | |
| 5,573,504 A | 11/1996 | Dorsey, III | |
| 5,643,230 A | 7/1997 | Linder | |
| 5,665,080 A | 9/1997 | Vandenberg | |
| 5,685,836 A | 11/1997 | DiPerna et al. | |

(Continued)

FOREIGN PATENT DOCUMENTS

WO  WO/98/52626  11/1998

*Primary Examiner* — Nicholas D Lucchesi
*Assistant Examiner* — Phillip Gray
(74) *Attorney, Agent, or Firm* — Lisa E. Winsor, Esq.

(57) ABSTRACT

An aspiration instrument includes a compliant protective guard for minimizing injury to internal organs and other soft tissue while removing fluids from the body cavity. The compliant protective guard may be constructed from foam, plastic or other like material, including polyethylene and polypropylene. A preferred embodiment of the protective guard takes the shape of a bell. The compliant guard may be connected with the aspiration instrument using adhesives, such as glue or epoxy, or with a snap or friction fit. The compliant guard may define a single opening in fluid communication with the yankauer. The compliant guard may also define a plurality of openings for removing fluids from the body.

9 Claims, 4 Drawing Sheets

U.S. PATENT DOCUMENTS

| | | |
|---|---|---|
| 5,728,078 A | 3/1998 | Powers, Jr. |
| 5,730,742 A | 3/1998 | Wojciechowicz |
| 5,752,286 A | 5/1998 | Wright |
| 5,807,353 A | 9/1998 | Schmitz |
| 5,817,052 A | 10/1998 | Johnson et al. |
| 5,876,384 A | 3/1999 | Dragan et al. |
| 5,921,970 A | 7/1999 | Vandenberg |
| 6,001,078 A | 12/1999 | Reckers |
| 6,086,587 A | 7/2000 | Hawk |
| 6,210,377 B1 | 4/2001 | Ouchi |
| 6,419,659 B1 | 7/2002 | Phelps et al. |
| 6,569,089 B1 | 5/2003 | Covington et al. |
| 6,575,944 B1 | 6/2003 | McNary et al. |
| 6,632,091 B1 | 10/2003 | Cise et al. |
| 6,638,253 B2 | 10/2003 | Breznock |
| 2002/0022796 A1 | 2/2002 | Lawrence et al. |
| 2002/0108614 A1 | 8/2002 | Schultz |
| 2005/0004535 A1 | 1/2005 | Schklair |

\* cited by examiner

COMPLIANT GUARD FOR USE WITH AN ASPIRATION INSTRUMENT

TECHNICAL FIELD

The present disclosure relates generally to a surgical aspiration instrument, and, more particularly, relates to an aspiration instrument which prevents damage to soft body tissue during use.

BACKGROUND

Aspiration instruments, sometimes known as yankauers, are necessary surgical tools used to remove fluids, such as blood, from a patient's body during surgical procedures. Conventional yankauers are constructed to have a handle and a body that define a fluid passageway for removing fluid from the surgical site. The handles and bodies of yankauers are manufactured in a variety of configurations and sizes for numerous applications. Long bodied yankauers are used to aspirate fluids from deep within a body cavity, while narrow bodied, fine tipped yankauers are appropriate for more precise fluid removal. The proximal end of the yankauer handle is configured to operatively connect with a vacuum source. The yankauer may be connected to the vacuum source by tube, hose, or the like.

Yankauers used to aspirate fluids from within the body cavity may come in contact with internal organs and other delicate tissue. These tissues are extremely sensitive and any minor contact with a yankauer can result in bruising or other injury to the tissue. The actual contact between the yankauer and the tissue does not need to be forceful to cause injury. Many prior art yankauers are made of rigid materials, including biocompatible metals, PVC, and other hard plastics. The use of rigid yankauers increases the risk of injury to the body tissues.

In addition to damage caused by incidental contact with the yankauer while aspirating the body cavity, delicate tissue may also be injured when the suction for removing fluids actually suctions a portion of the tissue into the distal end of the yankauer. Separating the tissue from the distal end of the yankauer, without releasing the suction may cause tearing or other serious injury to the tissue. The rigid materials from which the yankauers are constructed only exacerbate the injury.

Vents formed near the distal end of the yankauer are employed to help reduce the suction when the opening in the distal end becomes completely obstructed by tissue. Rather than continuing to suction on the tissue, the vents operate to divert the suction through openings in the side wall of the distal end of the yankauer. While the vents help to minimize damage to the tissue, the vents also reduce the efficiency of the yankauer in removing fluids from the body cavity. In addition to vents, yankauers may also be constructed with a valve member. The most simple valve member is an opening in the side of the handle. In order for the yankauer to suction through the opening in the distal end the opening must be covered. In the event tissue is suctioned into the yankauer the opening can be uncovered and the tissue may be separated from the yankauer. A valve member allows an operator to quickly stop the tissue from proceeding any further into the yankauer and cause and further damage. Unfortunately, once the operator realizes the tissue has been suctioned into the yankauer, the tissue has already incurred injury. In other valve member designs, the suction through the distal end of the yankauer is stopped by merely obstructing, or sealing, the end from the vacuum source. Simply obstructing the suction does not release the suction that already holds the tissue, increasing the potential for injury to the tissue when it is separated from hold of the yankauer. Therefore, it would be desirable to have a yankauer that utilizes a compliant protective guard to minimize risk of injury to organs or other body tissue.

SUMMARY

Accordingly, the present disclosure relates to an aspiration instrument having a compliant protective guard for minimizing injury to internal organs and other soft tissue while removing fluids from the body cavity. The compliant protective guard may be constructed from foam, plastic or other like material, including polyethylene and polypropylene. A preferred embodiment of the protective guard takes the shape of a bell. The compliant guard may be connected with the aspiration instrument using adhesives, such as glue or epoxy, or with a snap or friction fit. The compliant guard may define a single opening in fluid communication with the yankauer. The compliant guard may also define a plurality of openings for removing fluids from the body.

BRIEF DESCRIPTION OF THE DRAWINGS

Preferred embodiments of the present disclosure will be better appreciated by reference to the drawings wherein.

DESCRIPTION OF THE PREFERRED EMBODIMENTS

Figure 1:
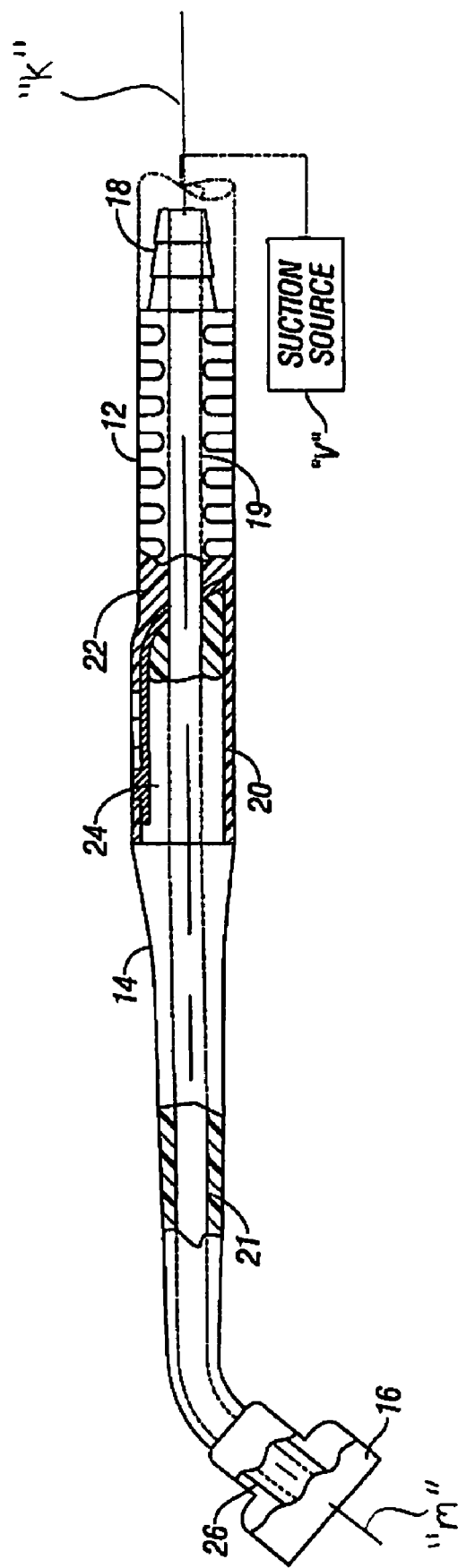
FIG. 1 is a side view of an aspiration instrument having a compliant protective guard in accordance with the principles of the present disclosure.

Referring now to the drawings wherein like reference numerals illustrate similar components throughout the several views. FIG. 1 illustrates one preferred embodiment of the present disclosure. Yankauer 10 is contemplated for use in surgical procedures requiring the aspiration of fluids of differing viscosities and compositions from body cavities. Examples of fluids of this type include blood, tissue fluid, tissue fragments, bone fragments, and rinsing fluids. Yankauer 10 consists of handle 12, elongated body member 14 extending from handle 12, and compliant protective guard 16 operatively connected with the end of the body member 14. In one preferred embodiment, handle 12 and body member 14 are individual components, however, the handle and the body member may also be integrated to form a single unit. Yankauer 10 may be formed of polymeric material and other plastics. Alternatively, yankauer 10 may be manufactured from a biocompatible metal such as titanium or stainless steel.

Yankauer 10 is operably connectable to a vacuum source "v" through the use of tubing, hosing, or other like material.

Handle 12 of yankauer 10 defines passageway 19 extending completely therethrough for the passage of fluids. Handle 12 defines proximal end 18, distal end 20 and middle portion 22, therebetween. Proximal end 18 of handle 12 is configured to be operably connected to a vacuum source "v". In the preferred embodiment, proximal end 18 is a standard male connection or barbed port to frictionally receive a hose, tube or the like. Alternatively, proximal end 18 may incorporate a luer connector to connect the tubing to handle 12. Middle portion 22 of handle 12 defines an elongated tubular section. Middle portion 22 is configured for gripping and handling of yankauer 10, and may include serrations or ribs on its outer surface to facilitate engagement of the user. Middle portion 22 of handle 12 may be configured with longitudinal fins as disclosed in copending U.S. patent application Ser. No. 10/536,545, incorporated herein by reference. Middle portion 22 of handle 12 may be configured with a valve member for controlling the suction delivered to the distal end of the yankauer. The valve member may be of any number of designs, including a slidable lever that operates to selectively obstruct passageway 19 through handle 12. Distal end 20 is configured to receive proximal end 24 of body member 14. Yankauers and yankauer handles are commonly known in the art and exist in various sizes and configurations. The subject matter of the present disclosure can be adapted to work with yankauer handles of all sizes and configurations.

Figure 2A:
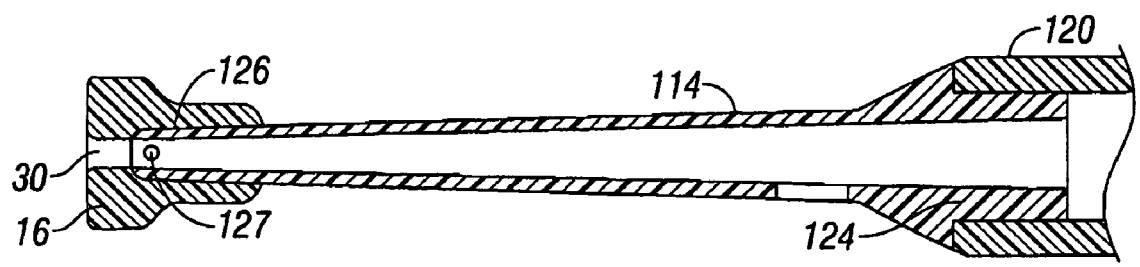
FIG. 2A is a side cross sectional view of a compliant protective guard mounted on an elongated body member of an aspiration instrument.
Figure 2B:
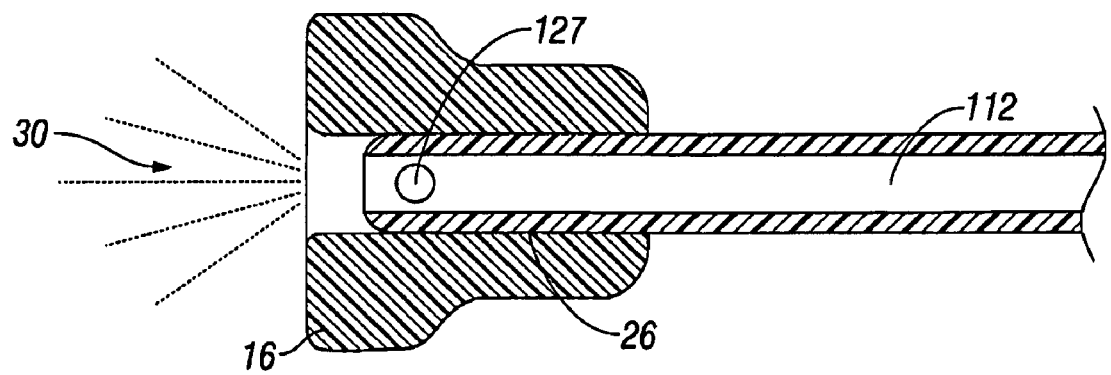
FIG. 2B is an enlarged cross sectional view of the distal end of the elongated body member shown in FIG. 2A.

Elongated body member 14 defines longitudinal axis "k" having passageway 21 therethrough in fluid communication with passageway 19 of handle 12 for the removal of fluids from the body cavity. Body member 14 has proximal end 24 and distal end 26. Distal end 26 of body member 14 defines an axial opening for receiving fluids from the operative site. Proximal end 24 of body member 14 is configured to be operably connected with distal end 20 of handle 12. Mechanical fasteners may also be employed to fluidly connect the two components. In one preferred embodiment, proximal end 24 is frictionally received by distal end 20 of handle 12, and is secured in place with an adhesive or mechanical fastener. With reference to FIGS. 2A and 2B, in an alternate embodiment, distal end 126 of body member 114 may further define vent 127 to prevent damage to aspirated tissue surfaces. In this embodiment, distal end 126 defines a mounting segment 126t arranged about an axis "m" in oblique relation with the longitudinal axis "k". As detailed above, vent 127 in distal end 126 of the body acts to reduce the suction applied to the body tissue when the tissue completely obstructs the fluid passageway. As noted above, yankauer handles are commonly known, as are methods for connecting handles to body members, body member configurations, and methods for venting yankauers so as to prevent damage to internal organs. All known connection and venting methods, as well as body member configurations, have been contemplated by this disclosure and are adaptable for use with the disclosed subject matter.

Protective guard 16 is secured to distal end 26 of body member 14. Protective guard 16 is configured to prevent damage to sensitive organs when aspirating a body cavity using yankauer 10. Protective guard 16 may be formed from an elastomeric material, foam, gel, gel bladder or the like. In one preferred application, protective guard 16 may be adapted to substantially deform upon contact with tissue, organs, etc. to substantially minimize or eliminate undesired manipulation or movement of the organ site. Preferred guard 16 material includes polypropylene and polyethylene. Protective guard 16 may be connected with body member 12 using any conventional means, including mechanical fasteners, friction fittings, and adhesives, such as glue and epoxy.

Protective guard 16 defines aperture 30 for receiving fluids from a body cavity. Aperture 30 is in fluid communication with passageway 21 of body member 14. The diameter of aperture 30 may be larger, smaller or the same size as the diameter of distal end 26 of body member 14, depending on the intended application of yankauer 10. The size and configuration of aperture 30 can be modified to regulate the amount of suction at the site of aspiration.

Guard 16 defines a generally bell shaped form wherein the distal end of guard 16 is larger than the proximal end of guard 16. The bell shape of guard 16 provides an increased surface area about aperture 30. The increased surface area provided by guard 16, coupled with the compliant material from which the guard 16 is formed, minimizes the possibility of damage to soft tissues contacted while aspirating the surgical site with a guarded yankauer. Guard 16 may define a porous structure which enables fluids from the surgical site to pass through the guard without entering aperture 30.

Figure 3A:
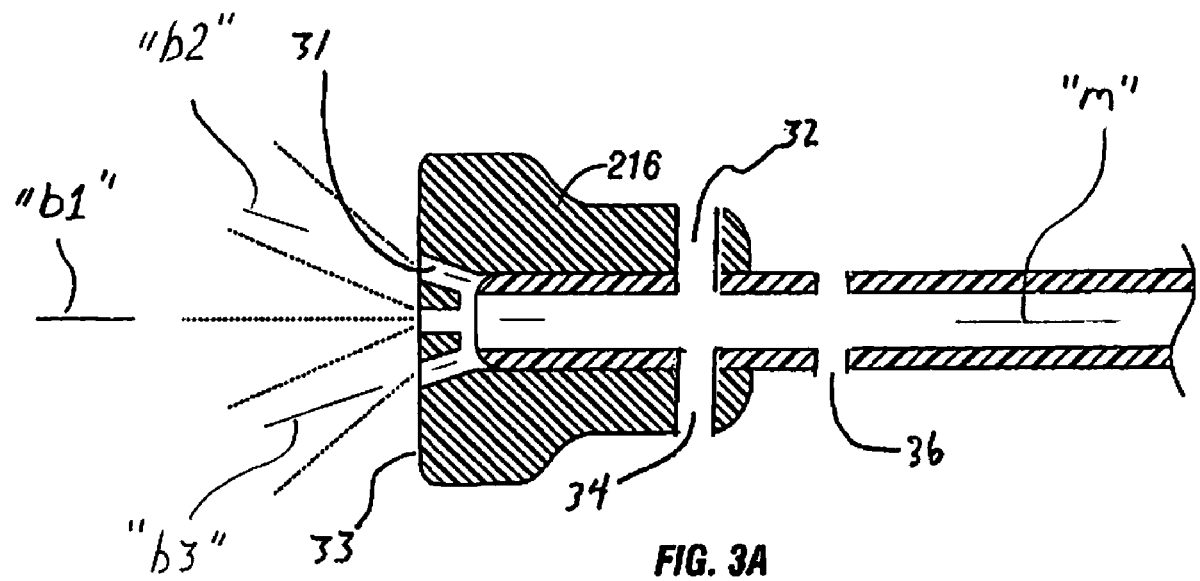
FIG. 3A is an enlarged side cross section view of a compliant protective guard having a plurality of openings and operably connected to the distal end of a yankauer.
Figure 3B:
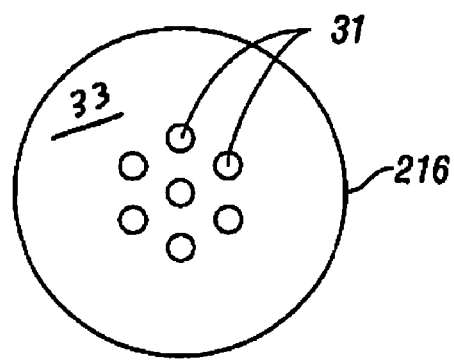
FIG. 3B is a frontal view of the compliant protective guard shown in FIG. 3A.

Referring now to FIGS. 3A and 3B, in an alternate embodiment, the distal end of guard 216 may define a plurality of passageways 31 rather than a single opening on the distal end of yankauer 200. Passageways 31 extend through distal face 33 of protective guard 216 and communicate with the axial opening of the yankauer. Passageways 31 are arranged about respective passageway axes "b1", "b2", "b3". Axes "b1" may be in general longitudinal alignments with axis "m" of the mounting segment while axes "b2", "b3" each intersect the axis "m". Increasing the size of the aperture in the distal end of the guard to allow for the removal of more fluids increases the possibility that internal organ tissue will be suctioned into the end of the yankauer. Increasing the number of openings within protective guard 216 while reducing the size of the openings provides a way to maintain aspiration capacity while reducing the potential for undesired entry of organ within the yankauer during aspiration procedures through a relatively large sized opening. Guard 216 and yankauer 200 may further include openings 32, 34 for venting the suction provided to yankauer 200. Yankauer 200 may also include second openings 36 for venting the suction.

Figure 4:
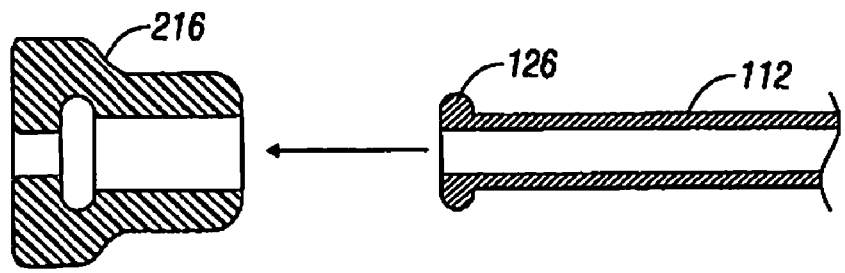
FIG. 4 is a cross sectional side view of a compliant protective guard having a snap fit connection with the distal end of a yankauer.

In another embodiment, now referring to FIG. 4, entry compliant guard 216 may be configured to snap fit onto modified distal end 126 of body member 112. Guard 216 may be configured to frictionally receive modified distal end 126 of body member. Guard 216 may be removable. Like previously disclosed guards, guard 216 may come in a variety of configurations and sizes.

Figure 5:
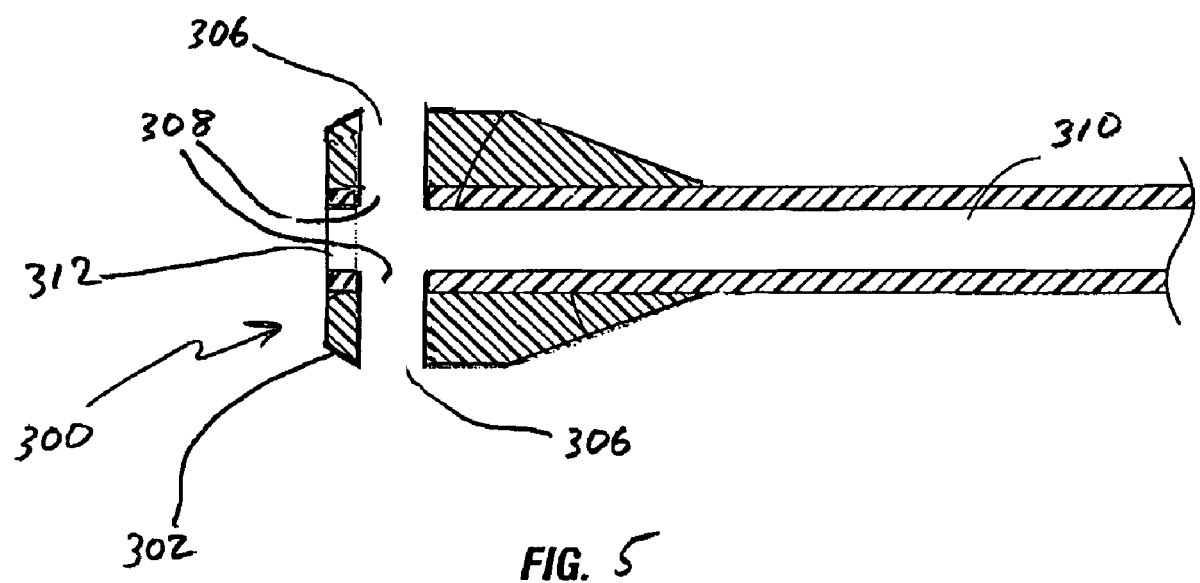
FIG. 5 is a cross sectional side view illustrating an alternate embodiment of a compliant protective guard of the present disclosure.

FIG. 5 illustrates another embodiment of the protective guard of the present disclosure. In accordance with this embodiment, protective guard 300 defines a reduced profile relative to the aforedescribed guards of FIGS. 1-4. In particular, distal end 302 of protective guard 300 defines a reduced cross-sectional dimension or diameter to facilitate manipulation through narrow passages in the body. The outer surface of distal end 302 may incorporate a taper as shown to facilitate positioning within the constricted passages. In addition, protective guard 304 includes a pair of aligned transverse bores 306 in communication with side openings 308 of body member 310 of the yankauer. Transverse bores 306 and side openings 308 provide secondary or alternate means for receiving fluids or tissue under suction and may supplement axial opening 312 of the yankauer in removing fluids and tissue. Alternatively, the yankauer may be devoid of axial opening 312 whereby aspiration is performed through transverse bores

306 and openings 308. Protective guard 300 is generally compliant and may be relatively soft to comply with the body tissue which it engages.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims append hereto.

What is claimed is:

1. An aspiration instrument for removing material from a body cavity, comprising:
    a single elongated member defining a longitudinal axis and having proximal and distal ends, the elongated member having a longitudinal conduit therethrough for passage of fluids; and
    a protective guard disposed adjacent the distal end of the elongated member, the protective guard defining at least two passageways extending completely through the protective guard in fluid communication with the longitudinal conduit to permit passage of fluids from the body cavity to the longitudinal conduit and at least one transverse bore, the protective guard comprising a relatively soft compliant material relative to the distal end of the elongated member and being adapted to substantially deform upon engagement with body tissue to substantially minimize the potential of damage to the body tissue, wherein the protective guard extends beyond the distal end of the elongated member;
    the elongate member further including a first side opening in alignment with the at least one transverse bore of the protective guard and a second side opening, the second side opening intermediate the proximal and distal ends of the elongate member and being located proximal of, and displaced from, the protective guard.

2. The aspiration instrument of claim 1 wherein the protective guard includes diametrically opposed first transverse bores and the elongate member includes diametrically opposed side openings in general alignment with respective opposed transverse bores.

3. An aspiration instrument for removing material from a body cavity, comprising:
    an elongated member defining a longitudinal axis and having proximal and distal ends, the elongated member having a longitudinal conduit therethrough for passage of fluids, the distal end having a distalmost axial opening in general longitudinal alignment with the longitudinal axis and in fluid communication with the longitudinal conduit wherein fluids entering the axial opening pass through the longitudinal conduit under suction pressure; and
    a protective guard disposed adjacent the distal end of the elongated member, the protective guard defining at least two passageways extending completely through the protective guard in fluid communication with the longitudinal conduit to permit passage of fluids from the body cavity to the longitudinal conduit, the protective guard comprising a relatively soft compliant material relative to the distal end of the elongated material and being adapted to substantially deform upon engagement with body tissue to substantially minimize the potential of damage to the body tissue, the protective guard includes:
        a first passageway, the first passageway arranged about a first axis in general alignment with the longitudinal axis of the elongated member and with the axial opening; and
        second and third passageways, the second and third passageways arranged about second and third passageways axes in intersecting relation with the longitudinal axis of the elongated member, wherein the second and third passageways extend through a distal end of the protective guard.

4. The aspiration instrument of claim 1 wherein the distal end of the elongated member defines a distalmost axial opening in alignment with the longitudinal axis and in communication with the longitudinal conduit wherein fluids entering the axial opening pass through the longitudinal conduit under suction pressure.

5. The aspiration instrument of claim 4 including a suction source in fluid communication with the longitudinal conduit of the elongated member to supply the suction pressure.

6. The aspiration instrument of claim 3 wherein the elongated member is a single elongated member.

7. The aspiration instrument of claim 6 wherein the elongated member includes a side opening between the proximal and distal ends thereof in communication with the longitudinal conduit, and displaced from the protective guard.

8. The aspiration instrument of claim 7 wherein the elongated member includes a supplemental side opening between the proximal and distal ends thereof in communication with the longitudinal conduit, and disposed within the protective guard.

9. The aspiration instrument of claim 3 including a suction source in fluid communication with the longitudinal conduit of the elongated member.

* * * * *